(12) United States Patent
Denyer et al.

(10) Patent No.: US 8,875,697 B2
(45) Date of Patent: Nov. 4, 2014

(54) DRUG DELIVERY APPARATUS AND METHOD

(75) Inventors: Jonathan S. H. Denyer, Chichester (GB); Ivan R. Prince, Chichester (GB); Ian Rabbetts, Hayling Island (GB)

(73) Assignee: RIC Investments, LLC, Wilmington, DE (US)

( * ) Notice: Subject to any disclaimer, the term of this patent is extended or adjusted under 35 U.S.C. 154(b) by 1323 days.

(21) Appl. No.: 12/176,582

(22) Filed: Jul. 21, 2008

(65) Prior Publication Data

US 2009/0025714 A1    Jan. 29, 2009

Related U.S. Application Data

(60) Provisional application No. 60/961,718, filed on Jul. 24, 2007.

(51) Int. Cl.
| | |
|---|---|
| A61M 11/00 | (2006.01) |
| A61M 15/00 | (2006.01) |
| A61M 16/00 | (2006.01) |
| B05B 17/06 | (2006.01) |
| B05D 7/14 | (2006.01) |
| B65D 83/06 | (2006.01) |

(52) U.S. Cl.
CPC .......... *A61M 15/00* (2013.01); *A61M 2205/502* (2013.01); *A61M 2016/0036* (2013.01); *A61M 15/002* (2013.01); *A61M 15/0085* (2013.01); *A61M 15/0021* (2013.01); *A61M 2202/04* (2013.01)
USPC .............. 128/200.16; 128/200.23; 128/203.15

(58) Field of Classification Search
USPC .............. 128/203.12, 203.15, 203.21, 203.23, 128/203.24, 204.18, 204.21, 204.23, 128/204.25–204.28, 205.23, 128/200.11–200.24, 200.26, 128/205.24–205.25, 206.29, 207.12, 128/207.14, 207.16; 604/68–72
See application file for complete search history.

(56) References Cited

U.S. PATENT DOCUMENTS 4,674,491 A  *  6/1987  Brugger et al. .......... 128/200.14
5,724,959 A  *  3/1998  McAughey et al. ..... 128/203.15
(Continued)

FOREIGN PATENT DOCUMENTS

| GB | 2395437 A * | 5/2004 | ............ A61M 15/00 |
| WO | WO 2004041336 A1 * | 5/2004 | |
| WO | WO 2006013952 A1 * | 2/2006 | |

OTHER PUBLICATIONS

International Preliminary Report on Patentability for PCT/GB2008/002538.*

*Primary Examiner* — (Jackie) Tan-Uyen T Ho
*Assistant Examiner* — Mark K Han

(57) ABSTRACT

A drug delivery apparatus includes a mouthpiece portion having an internal conduit for delivering an aerosol including the drug to the patient. The internal conduit has an inlet end and a mouthpiece end that is structured to be received in the patient's mouth. The mouthpiece portion is structured to operate at a substantially fixed inhalation flow rate when the patient inhales through the mouthpiece end. The apparatus further includes an aerosol generator for generating the aerosol from a drug supply and injecting the aerosol into a first region within the mouthpiece portion located between an outlet of the aerosol generator and the inlet end of the conduit. The mouthpiece portion also includes a flow accelerating mechanism that causes a localized flow rate at the first region to be greater than the inhalation flow rate. A method is also provided that increases the local flow rate within the mouthpiece portion.

16 Claims, 7 Drawing Sheets

(56) References Cited

U.S. PATENT DOCUMENTS

| | | | |
|---|---|---|---|
| 5,829,434 A * | 11/1998 | Ambrosio et al. | 128/203.15 |
| 5,957,124 A | 9/1999 | Lloyd et al. | |
| 6,039,042 A * | 3/2000 | Sladek | 128/200.23 |
| 6,347,629 B1 * | 2/2002 | Braithwaite | 128/203.15 |
| 6,705,312 B2 * | 3/2004 | Tanaka et al. | 128/200.14 |
| 6,849,060 B1 * | 2/2005 | Brooks et al. | 604/58 |
| 7,107,987 B2 * | 9/2006 | Sundaram et al. | 128/200.23 |
| 2006/0120968 A1 * | 6/2006 | Niven et al. | 424/45 |
| 2006/0243277 A1 | 11/2006 | Denyer et al. | |
| 2007/0227534 A1 * | 10/2007 | Nobutani et al. | 128/200.14 |
| 2010/0154794 A1 * | 6/2010 | Valentin | 128/203.15 |
| 2011/0155129 A1 * | 6/2011 | Stedman et al. | 128/200.23 |

* cited by examiner

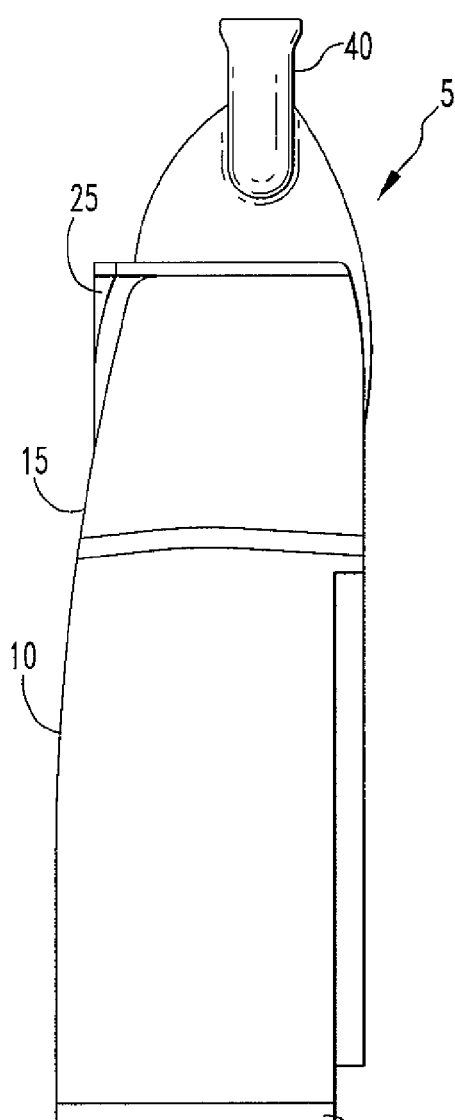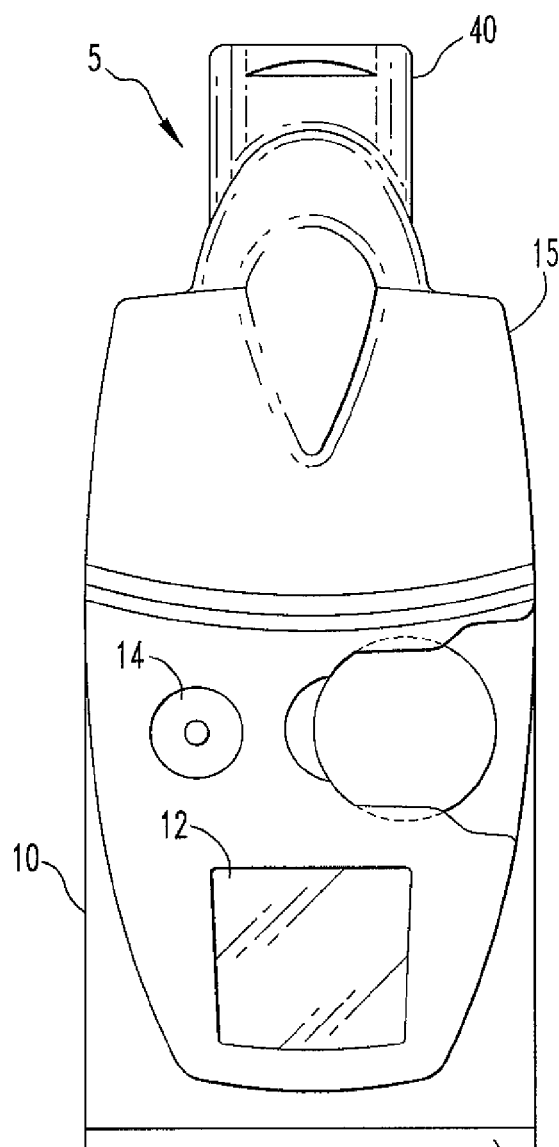

DRUG DELIVERY APPARATUS AND METHOD

CROSS-REFERENCE TO RELATED APPLICATIONS

This application claims priority under 35 U.S.C. §119(e) from provisional U.S. patent application No. 60/961,718 filed Jul. 24, 2007, the entire contents of which are incorporated herein by reference.

FIELD OF THE INVENTION

The present invention relates to devices that deliver drugs to a patient in aerosol form, commonly referred to as nebulizers, and in particular to a drug delivery apparatus and method that improves performance by reducing the particle size of the drug included in the aerosol.

BACKGROUND OF THE INVENTION

A number of devices are available for delivering a drug into the lungs of a patient. Once such device is a nebulizer, which is a device that is used for converting a liquid, such as a liquid medication, into an aerosol which is then inhaled by the patient, typically through a mouthpiece. A number of different types of nebulizers exist, such as, without limitation, jet nebulizers and ultrasonic nebulizers. A typical jet nebulizer uses compressed air to generate the aerosol from the liquid. One type of ultrasonic nebulizer employs acoustic waves having an ultrasonic frequency that are directed to a point on the surface of the liquid that is to be converted into an aerosol. At the point on the surface of the liquid where these ultrasonic waves converge, they will produce capillary waves that oscillate at the frequency of the ultrasonic waves. If the amplitude of the waves is large enough, the peaks of the capillary waves will break away from the liquid and be ejected from the surface of the liquid in the form of droplets, thereby forming the aerosol. A device that is often used for generating ultrasonic waves in an ultrasonic nebulizer is a piezoelectric transducer (such as a piezoelectric crystal), which vibrates and generates ultrasonic waves in response to an applied electric field. In another type of ultrasonic nebulizer, the liquid that is to be converted into an aerosol is forced through a mesh (thereby creating liquid droplets) by the vibration of a piezoelectric crystal acting upon a horn. In this type of ultrasonic nebulizer, the gauge of the mesh determines the size of the droplets which are created to form the aerosol.

Conventional nebulizer systems provide a continuous aerosol/drug output, and thus the amount of drug inhaled is dependent upon the patient's breathing pattern. The duty cycle of the patient's breathing pattern is typically 40:60. This means that the patient spends 40 percent of a single respiratory cycle in inspiration and 60 percent of the time in expiration. Thus, 60 percent of the drug delivered from the nebulizer will be wasted to the environment during expiration. In addition, the breathing pattern of a single patient over the course of a treatment will vary. In order to address these issues, more sophisticated nebulizer systems have been developed which adapt the delivery of aerosol to the patient's breathing pattern, delivering medication only when the patient is inhaling through the mouthpiece.

Adaptive nebulizer systems as just described have been developed which are capable of a number of different modes of operation. For example, one such system is capable of operating in either a tidal breathing mode and a target inhalation mode.

In the tidal breathing mode (TBM), the nebulizer system monitors the flow and inhalation time for the first few breaths (.e.g., three breaths) of each treatment. This information is used to predict how long the next breath is going to be. Once this has been calculated, aerosol is emitted into the beginning of the next inhalation. The prediction is updated after each new breath to ensure accuracy through the whole of the treatment. In a typical implementation, the device will emit aerosol into approximately 50 to 80 percent of each inhalation. In this mode, very little of the medication is wasted to atmosphere because the aerosol is emitted only when the patient is breathing in.

In the target inhalation mode (TIM), the nebulizer system encourages each patient to inhale for as long as they can, as this can result in a greater amount of the medication getting into the lungs, and can also reduce the treatment time. In particular, the patient is instructed to breathe in through the mouthpiece until a signal, such as vibration through the mouthpiece, is provided. The time between the start of the breath and the signal is called the target inhalation time—in other words, how long the patient should inhale. At the beginning of the first treatment, the target inhalation time is set to predetermined time, such as three seconds. If the patient is able to inhale past the target inhalation time, then the target inhalation time for the next breath is made a little longer. In this way, the duration of the breath is gradually increased until the patient reaches a target inhalation time that is suited to his/her own capabilities. If the patient is not able to inhale past the target inhalation time, then the target inhalation time for the next breath is made a little shorter. Also, there is always a gap, such as a two second gap, between the end of aerosol production and the target inhalation time signal to ensure that substantially all of the aerosol reaches the patient's lungs. One particular implementation of a nebulizer system which is able to operate in a target inhalation mode is described in United States Patent Application Publication No. 2006/0243277, entitled "Inhalation Method and Apparatus" and assigned to the assignee hereof, the disclosure of which is incorporated herein by reference.

Furthermore, the target inhalation mode is typically operated at a fixed inhalation flow rate, e.g., 15 l/min, which is lower than the inhalation flow rate of the tidal breathing mode, which can be as high as 80 l/min. It has been discovered that this difference in flow rates, particularly in the locality where the aerosol plume is generated, results in the aerosol particle size in the target inhalation mode being larger than the aerosol particle size in the tidal breathing mode. As will be appreciated by those of skill in the art, the smaller the particle size of the aerosol, the greater the lung deposition of the medication, as less medication will get trapped in the patient's upper airway and more medication will reach the periphery of the patient's lungs. Thus, it would be advantageous to be able to reduce the particle size of the aerosol that is generated by a nebulizer system that is operating at a given, fixed inhalation flow rate, such as a nebulizer system that is operating in the target inhalation mode at a 15 l/min inhalation flow rate, and, as a result, enhance lung deposition.

SUMMARY OF THE INVENTION

In one embodiment, the present invention provides a drug delivery apparatus for delivering an aerosol including a drug to a patient. The apparatus includes a mouthpiece portion having an internal conduit for delivering the aerosol to the patient (by inhalation through the internal conduit). The internal conduit has an inlet end and a mouthpiece end opposite the inlet end that is structured to be received in the mouth of the patient. The mouthpiece portion is structured to operate at a substantially fixed inhalation flow rate, such as through a control valve provided in the mouthpiece portion, when the patient inhales through the mouthpiece end. The apparatus further includes an aerosol generator for generating the aerosol from a supply of the drug and injecting the aerosol into a first region within the mouthpiece portion located between an outlet of the aerosol generator and the inlet end of the internal conduit. In addition, the mouthpiece portion includes a flow accelerating mechanism that causes a localized flow rate at the first region to be greater than the inhalation flow rate.

The flow accelerating mechanism may take on a number of different forms. For example, and without limitation, the flow accelerating mechanism may be an insert having an orifice that is inserted within the internal conduit at the inlet end. In one particular embodiment, the internal conduit is generally cylindrically shaped and has a cross sectional diameter, and the orifice is generally circular and has an orifice diameter, wherein the orifice diameter is smaller than the cross sectional diameter. In another particular embodiment, the internal conduit is generally cylindrically shaped and has a cross sectional diameter, and the orifice is defined by a first arcuate edge located opposite a second arcuate edge, wherein a degree of curvature of the first arcuate edge is greater than a degree of curvature of the second arcuate edge. Preferably, the second arcuate edge is located closer to an outer edge of a top surface of the insert than the first arcuate edge, and the first arcuate edge is located closer to a center of the insert than the second arcuate edge. In another embodiment, the flow accelerating mechanism is formed integrally as part of the internal conduit. In this embodiment, the flow accelerating mechanism may be an end portion of the internal conduit at the inlet end, wherein the end portion has an orifice formed therein. Alternatively, the internal conduit may be generally cone shaped and taper outwardly from the inlet end.

In another embodiment, the present invention provides a method of delivering an aerosol including a drug to a patient that includes providing a mouthpiece portion including an internal conduit for delivering said aerosol to said patient, wherein the internal conduit has an inlet end and a mouthpiece end opposite the inlet end that is structured to be received in the mouth of the patient. The mouthpiece portion is structured to operate at an inhalation flow rate when the patient inhales through the mouthpiece end. The method further includes generating the aerosol from a supply of the drug and injecting the aerosol into a first region within the mouthpiece portion located between a location at which said aerosol is generated and the inlet end of the internal conduit, and causing a localized flow rate within the mouthpiece portion at the first region to be greater than the inhalation flow rate.

In still another embodiment, the present invention provides a method of delivering an aerosol including a drug to a patient including providing a mouthpiece portion including an internal conduit for delivering the aerosol to the patient, wherein the internal conduit has an inlet end and a mouthpiece end opposite the inlet end that is structured to be received in the mouth of the patient. The mouthpiece portion is structured to operate at an inhalation flow rate when the patient inhales through the mouthpiece end. The method further includes detecting the commencement of inhalation by the patient through the mouthpiece end, generating the aerosol from a supply of the drug and injecting the aerosol into a first region within the mouthpiece portion located between a location at which the aerosol is generated and the inlet end of the internal conduit for at least a portion of the time that the patient in inhaling through the mouthpiece end, and causing a localized flow rate within the mouthpiece portion at the first region to be greater than the inhalation flow rate during the generating step. Finally, the method includes signaling the patient to cease inhalation through the mouthpiece end after a pre-set period of time has elapsed from the detection of the commencement of inhalation, and adjusting the pre-set period of time for subsequent inhalations through the mouthpiece end based upon a time difference (positive or negative) between a time that the signaling step is commenced and a time at which the patient actually ceases inhalation through the mouthpiece end.

Therefore, it should now be apparent that the invention substantially achieves all the above aspects and advantages. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

The accompanying drawings illustrate presently preferred embodiments of the invention, and together with the general description given above and the detailed description given below, serve to explain the principles of the invention. As shown throughout the drawings, like reference numerals designate like or corresponding parts.

FIG. 1 is a front elevational view and FIG. 2 is a left side elevational view of a nebulizer device according to one embodiment of the invention;

DESCRIPTION OF THE EXEMPLARY EMBODIMENTS

Figure 3:
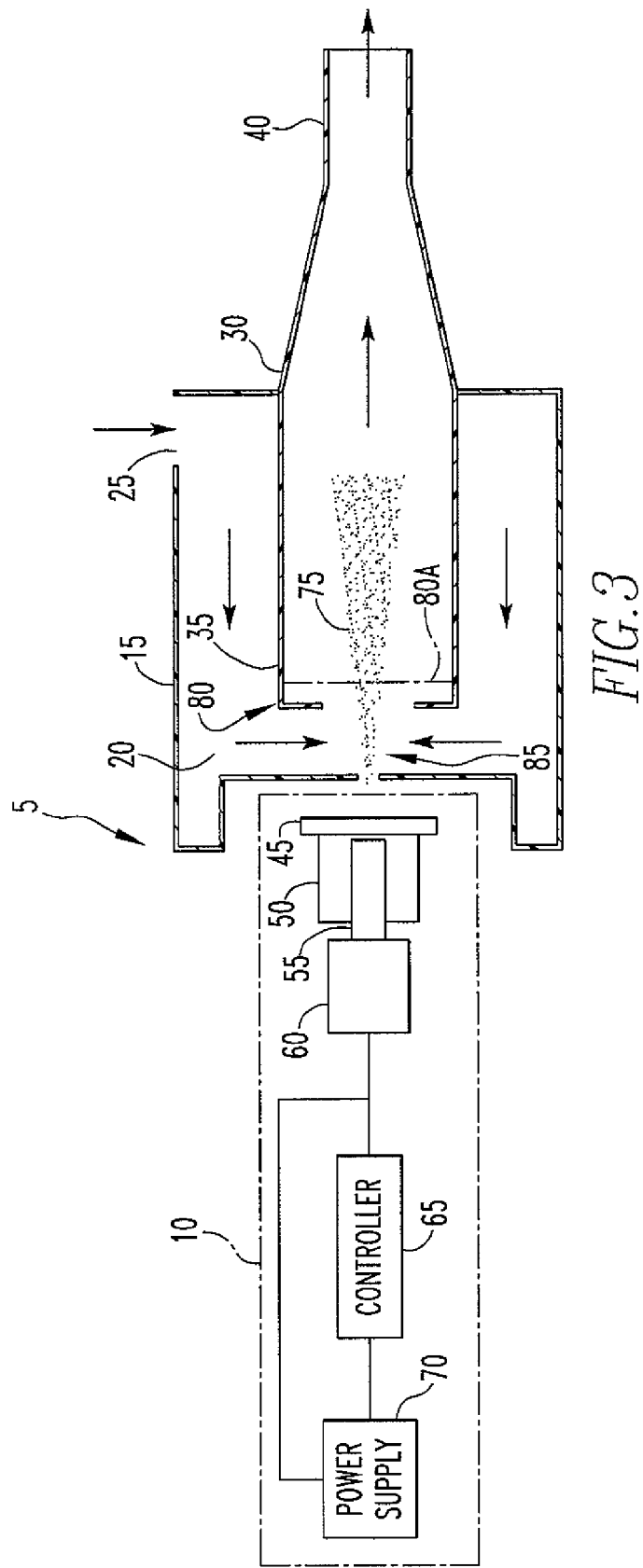
FIG. 3 is a schematic diagram of the nebulizer device of FIGS. 1 and 2.

FIG. 1 is a front elevational view and FIG. 2 is a left side elevational view of a nebulizer device 5 according to one embodiment of the invention. FIG. 3 is a schematic diagram of the nebulizer device 5 which shows selected components thereof in a simplified or symbolic form. The nebulizer device 5 functions as a drug delivery system for delivering a drug in the form of an aerosol into the lungs of a patient. The nebulizer device 5 includes a main housing 10 which houses certain components (shown in FIG. 3 and described below) of the nebulizer device 5 and a mouthpiece portion 15 which is removeably attached to the main housing 10. Of course, the nebulizer device could have a variety of other outputs other than a mouthpiece. For instance, the device may be connected to an endotracheal tube, a mask, or a respiratory support device. As shown schematically in FIG. 3, the mouthpiece portion 15 includes a chamber 20 which, when the mouthpiece portion 15 is attached to the main housing 10, is structured to receive the aerosol that is generated by the components in the main housing 10 as described in more detail below. The chamber 20 includes an air inlet 25 and an internal conduit 30 having an inlet end 35 and a mouthpiece end 40 that is structured to be received in the mouth of the patient. As shown by the arrows in FIG. 3, when the patient places his or her mouth on the mouthpiece end 40 and inhales, air is caused to flow into the chamber 20 from the air inlet 25 and through the internal conduit 30 from the inlet end 35 to the mouthpiece end 40. As will be appreciated, that air stream carries the aerosol that is generated in the manner described below into the lungs of the patient.

As seen in FIG. 3, the main housing 10 includes a mesh plate 45 (including a plurality of miniature holes therein), a reservoir 50 for holding the liquid (drug) to be converted into an aerosol a horn 55, and a piezoelectric transducer 60 operatively coupled to the horn 55. The main housing 10 also includes a controller 65, which may be a microprocessor, microcontroller, or some other suitable electronic control device or circuitry, and a power supply 70, which preferably is a rechargeable battery. The horn 55 is located close to the rear face of the mesh plate 45 and may be caused to vibrate by the piezoelectric transducer 60 under the control of the controller 65, with the power to drive the piezoelectric transducer 60 being provided by the power supply 70. The liquid in the reservoir 50 is in fluid contact with the rear face of the mesh plate 45. When the piezoelectric transducer 60 is caused to vibrate, it drives the horn 55 to vibrate in the region of the mesh plate 45. As a result of such vibration of the horn 55, the liquid from the reservoir 50 is forced through the holes of the mesh plate 45, thereby generating an aerosol plume 75 that is injected into the chamber 20 and ultimately into the internal conduit 30. As seen in FIG. 1, the main housing 10 includes an LCD 12 for providing information to the patient about the treatment and operation of the nebulizer device 5, and button 14 for providing input for controlling various aspects of the nebulizer device 5.

According to one aspect of an embodiment of the invention, the internal conduit is provided with a flow accelerating mechanism 80 at the inlet end 35 of the internal conduit 30. The flow accelerating mechanism 80 functions to cause the local flow rate in the region 85 where the aerosol plume 75 is injected into the chamber 20 to be increased (relative to the inhalation flow rate at which the mouthpiece portion 15 is structured to operate). For example, if the nebulizer device 5 were operating in a mode (e.g., a TIM mode, TBM mode) which employs a fixed inhalation flow rate through the mouthpiece portion 15, such as in the range of 10-25 l/min, the flow accelerating mechanism 80 would cause the local flow rate in the region 85 to be higher than 15 l/min, such as in the range of 100-500 cm/sec (the actual flow rate will depend on the structure of the flow accelerating mechanism 80). The increased flow rate in the region 85 promotes more effective mixing of the inhalation flow and the aerosol particles, thereby reducing the particle size of the aerosol. As described elsewhere herein, reducing the particle size of the aerosol is advantageous as it enhances lung deposition of the medication.

Figure 4A:
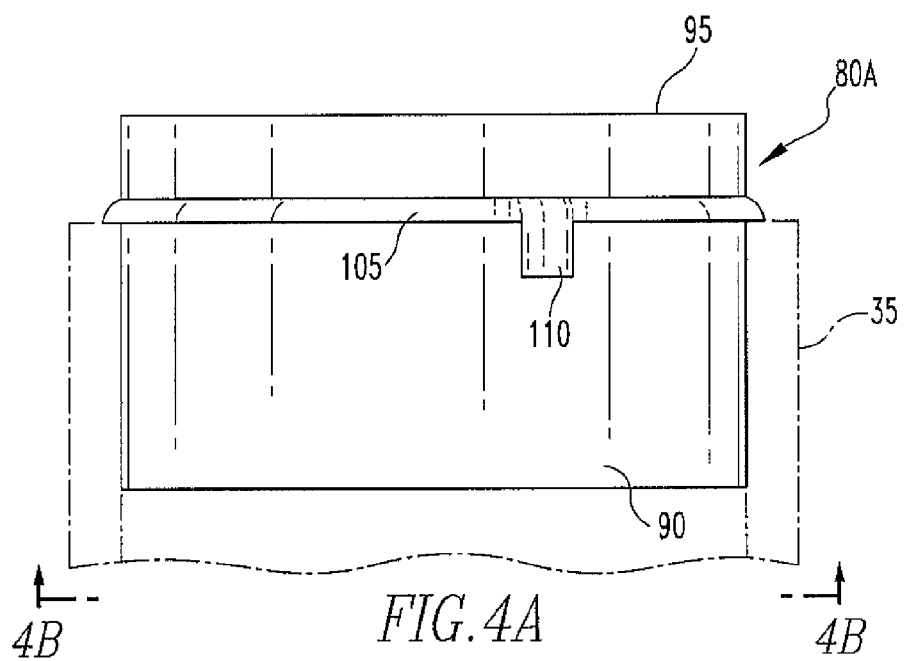
FIG. 4A is a side elevational view and FIG. 4B is a top plan view of an insert forming a flow accelerating mechanism according to one embodiment of the present invention.
Figure 4B:
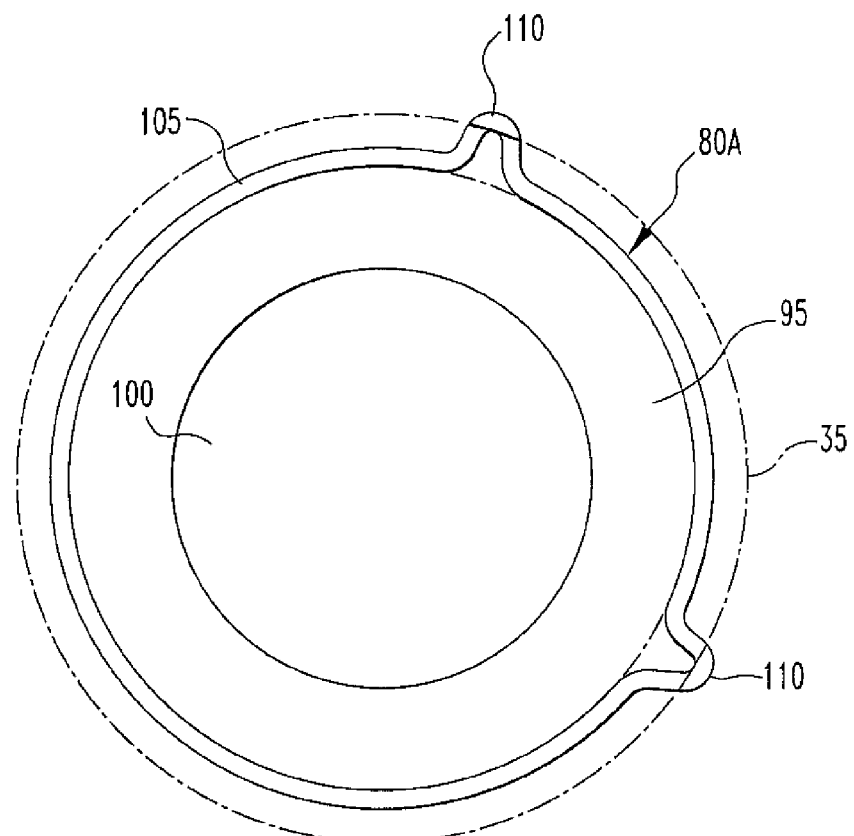

In one particular embodiment, the flow accelerating mechanism 80 is an insert 80A as shown FIGS. 4A and 4B (and in FIG. 3) which is adapted to be inserted and held within the inlet end 35 of the internal conduit 30 of the mouthpiece portion 15. Of course, the flow accelerating mechanism 80 may have a variety of other configurations. For instance, the flow accelerating mechanism 80 may be formed integrally with the inlet end 35. Alternatively, the flow accelerating mechanism may be formed as a cap fitted over the inlet end, or even configured as a cartridge slid into place through an opening in one side of the inlet end 35. As seen in FIGS. 4A and 4B, the insert 80A has a generally cylindrical shape including a body 90 adapted to be received within the inlet end 35 and a top surface 95. In addition, the insert 80A includes an orifice 100 having a circular shape. It is the orifice 100 that causes the flow rate in the region 85 where the aerosol plume 75 is injected into the chamber 20 to be increased relative to the inhalation flow rate in the rest of the chamber 20. The insert 80A also includes an outer lip 105 extending around the outer periphery of the body 90 and a pair of flanges 110 extending from the outer periphery of the body 90. The outer lip 105 is structured to rest on top of and the flanges 110 are structured to fit over the outside of the inlet end 35 to hold the insert 80A in place.

Figure 5:
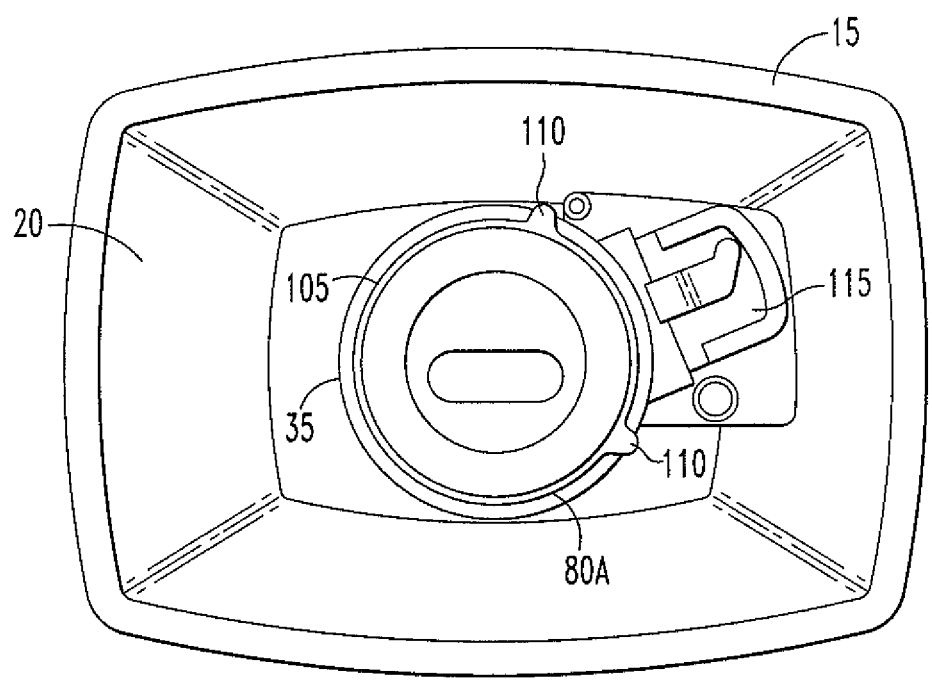
FIG. 5 is an end view of a mouthpiece portion forming a part of the nebulizer device shown in FIGS. 1 and 2 which includes the insert according to an aspect of the invention.

As will be appreciated, the insert 80A shown in FIGS. 4A and 4B assumes that the outer edge of the inlet end 35 of the internal conduit 30 lies in a plane that is perpendicular to the longitudinal axis of the internal conduit 30 as is shown in FIG. 3. However, that may not always be the case. For example, the outer edge of the inlet end 35 may lie in a plane that is oriented at an angle that is less than 90 degrees with respect to the longitudinal axis of the internal conduit 30 as shown in mouthpiece portion 15' shown FIG. 6. The outer edge of the inlet end 35 may be provided in that manner to, for example, compensate for an uneven flow within the chamber 20 caused by a valve 115 for controlling inhalation flow rate that is offset within the chamber 20 (as shown in FIG. 5). In such a case, the flow accelerating mechanism 80 will preferably be in the form of an insert 80B shown in FIG. 7. As seen in FIG. 7, the outer lip 105 is oriented at an angle with respect to the top surface 95. That angle will compensate for the outer edge of the inlet end 35 so that the top surface 95 will be generally perpendicular to the longitudinal axis of the internal conduit 30 when the insert 80B is inserted within the inlet end 35 of the internal conduit 30.

Figure 8:
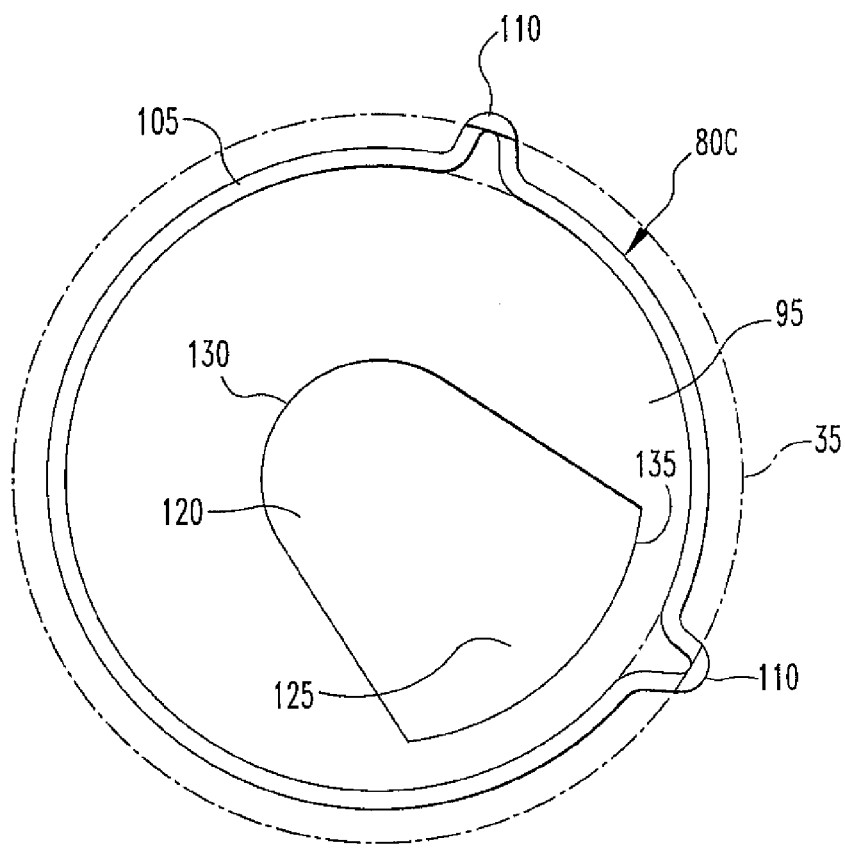
FIG. 8 is a top plan view of an insert forming a flow accelerating mechanism according to still another embodiment of the present invention.

In addition, in situations where there is an uneven flow within the chamber 20 caused by, for example, a valve 115 for controlling inhalation flow rate that is offset within the chamber 20 (as shown in FIG. 5), it has been found that if an insert such as 80A or 80B is employed, there is a tendency for the medication in the aerosol to become deposited at a particular location on the insert 80A or 80B. Specifically, it has been found that medication tends to become deposited on the lower right hand quadrant of the insert 80A or 8OB (in the orientation of FIG. 5) when the valve 115 is located in the position shown in FIG. 5. Thus, in order to compensate for this phenomenon, an insert 80C according to an alternate embodiment of the invention as shown in FIG. 8 may be employed. The insert 80C includes an orifice 120 that, instead of being circular in shape, has the shape shown in FIG. 8. In particular, the orifice 120 has an enlarged portion 125 that located in the area where medication would normally tend top become deposited in order to allow that medication to instead pass through to the internal conduit 30. The orifice 120 is defined by a first arcuate edge 130 located opposite a second arcuate edge 135 wherein the degree of curvature of the first arcuate edge 130 is greater than the degree of curvature of the second arcuate edge 135. In addition, as seen in FIG. 8, in the preferred embodiment, the second arcuate edge 135 is located closer to the outer edge of the top surface 95 than the first arcuate edge 130, which tends to be located closer to the center of the insert 80C.

Figure 9:
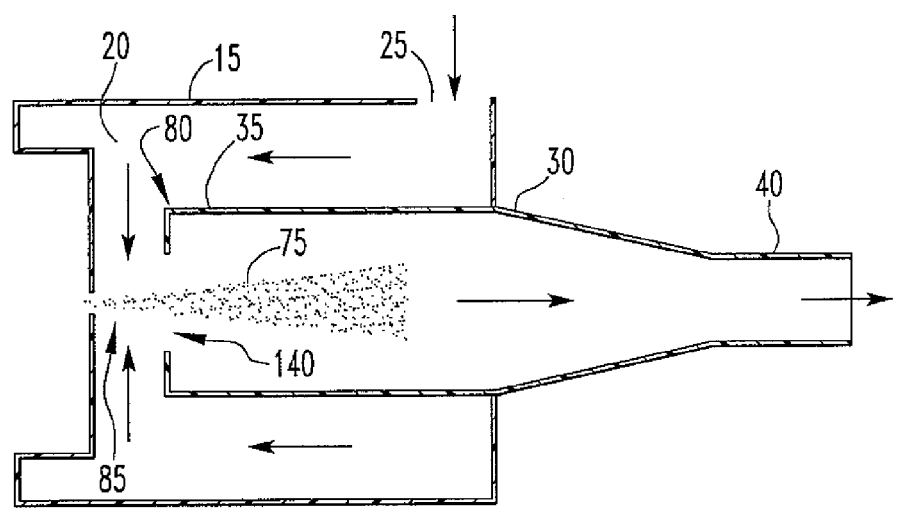
FIG. 9 is a schematic diagram of a further alternative embodiment of a mouthpiece portion that may be used in the nebulizer device shown in FIGS. 1 and 2.

In an alternative embodiment, rather than the flow accelerating mechanism 80 being in the form of a separate insert 80A, 80B, or 80C as just described, it may be formed integrally with the internal conduit 30 as shown in FIG. 9 in the form of an orifice 140 provided in the inlet end 35 of the internal conduit 30. In this embodiment the orifice 140 preferably has a maximum width (e.g., diameter in the case of a circular orifice 140) that is less than the diameter of the cylindrically shaped internal conduit 30.

Figure 6:
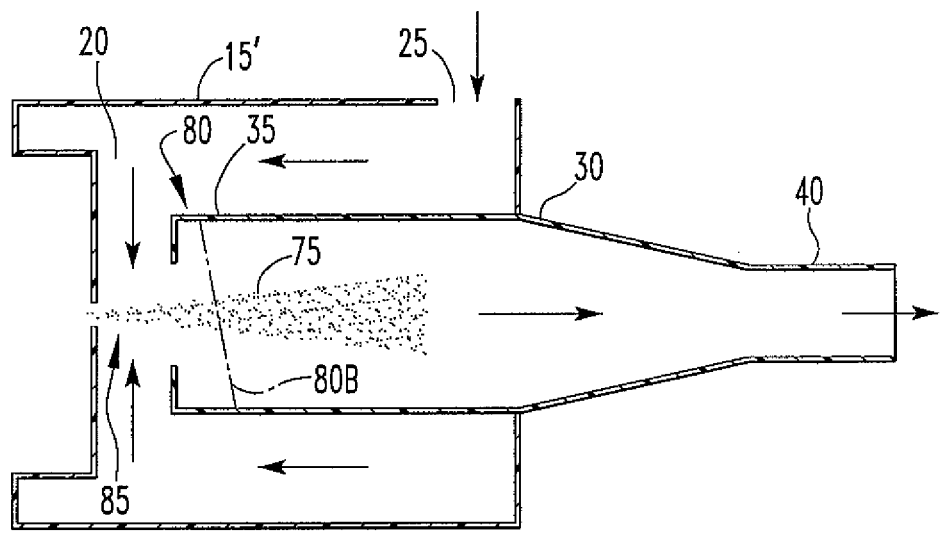
FIG. 6 is a schematic diagram of an alternative embodiment of a mouthpiece portion that may be used in the nebulizer device shown in FIGS. 1 and 2.
Figure 7:
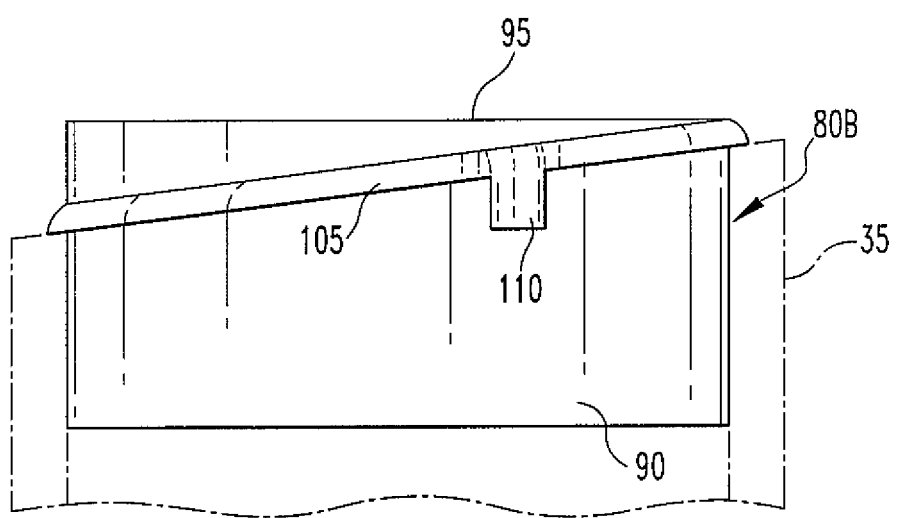
FIG. 7 is a side elevational view of an insert forming a flow accelerating mechanism according to another embodiment of the present invention.
Figure 10A:
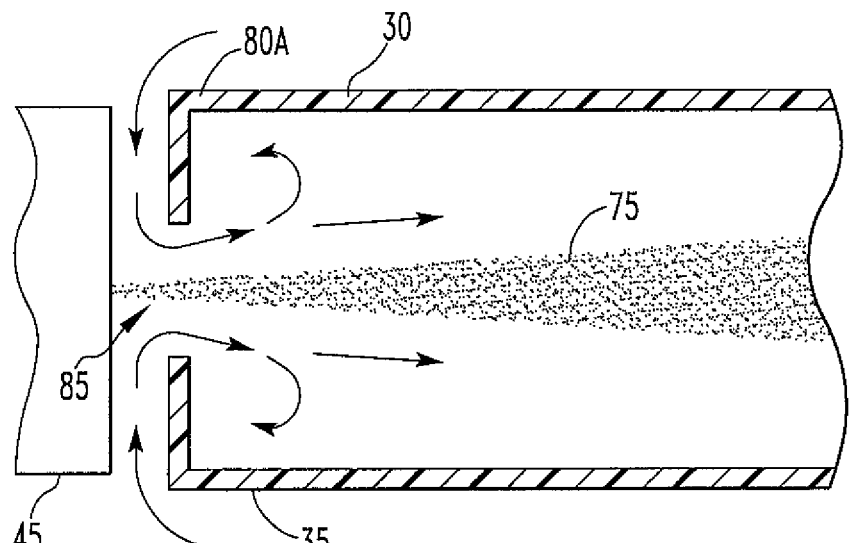
FIG. 10A is a schematic diagram which illustrates aerosol flow in one embodiment of an internal conduit of a mouthpiece portion that may be used in the nebulizer device shown in FIGS. 1 and 2.
Figure 10B:
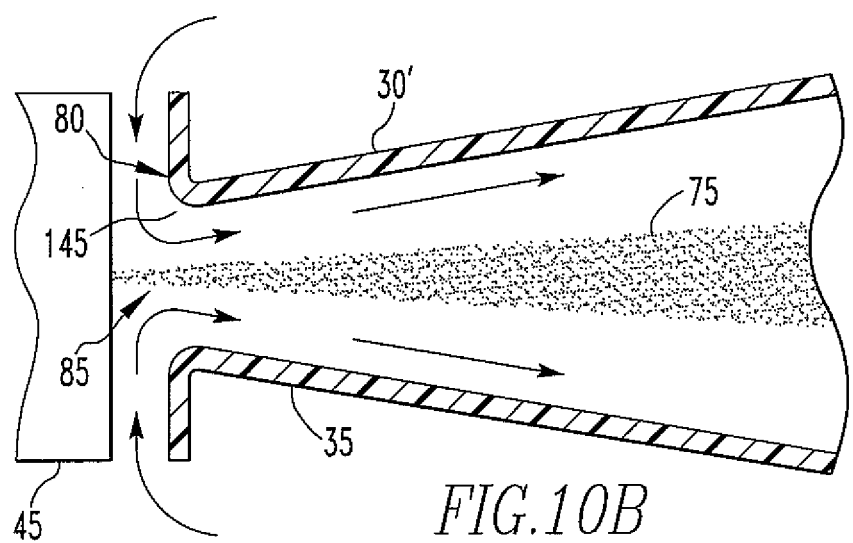
FIG. 10B is a schematic diagram which illustrates aerosol flow in another embodiment of an internal conduit of a mouthpiece portion that may be used in the nebulizer device shown in FIGS. 1 and 2.

Moreover, when the internal conduit 30 of the mouthpiece portion 15 is shaped as shown in FIGS. 3, 6 and 9 (i.e., generally cylindrical), the vortex spread from the orifice 100 of the insert 80A or 80B or the orifice 120 of the insert 80C may tend to cause medication to be deposited on the inside of the internal conduit 30. This tendency is illustrated schematically in FIG. 10A. FIG. 10B shown an internal conduit 30' according to an alternative embodiment that may form part of the mouthpiece portion 15. As seen in FIG. 10B, the internal conduit 30' is tapered outwardly, preferably in the form of a cone, beginning at the inlet end 35. In this embodiment, like the embodiment shown in FIG. 9, the flow accelerating mechanism 80 is preferably formed integrally with the internal conduit 30' in the form of a circular orifice 145 provided in the inlet end 35 of the internal conduit 30' (it will be understood that alternatively an insert as described elsewhere herein may also be used). The orifice 145 thus has a diameter that is equal to the smallest diameter of the cross-section of the tapered, preferably cone shaped internal conduit 30'. The tapered, preferably cone shaped internal conduit 30' reduces turbulence just inside the inlet end 35 and as a result reduces deposition of medication on the inside of the internal conduit 30'.

In operation, the present invention also provides a method of delivering aerosol to a patient. Specifically, the aforementioned device may be utilized by coupling the device to the airway of the patient such as by placing a mouthpiece into the patient's mouth, a mask over the patient's mouth and/or nose, connecting the device to an endotracheal tube, or connecting the device to a respiratory circuit. In one embodiment, the outlet end is a mouthpiece configured to be received in the mouth of the user. The mouthpiece is sized and configured to achieve a desirable flow rate as the patient inhales. Aerosol is generated from a supply of drug and injected into a first region of the mouthpiece. The airflow is accelerated through a localized region of the mouthpiece. In one embodiment, the aerosol generation is initiated in response to a sensor (e.g. flow rate sensor) detecting the breathing pattern including inhalation and exhalation. The nebulizer device includes a processor and a memory which stores a pre-set inhalation time goal. Once the patient has reached the pre-set inhalation time, a signal may be provided to the patient indicating that the patient should cease inhalation. As the patient utilizes the device, the patient's performance may be monitored by the processor, and the processor may adjust the pre-set inhalation time period based upon the detected patient performance. For instance, in the event that the patient is not able to meet the inhalation time goal, the pre-set inhalation time may be decreased. Alternatively, if the patient has excess capacity, the pre-set inhalation time period may be increased. Although a variety of different methods may be employed to determine the patient's performance, one method of determining the patient's performance is based on how quickly the patient ceases inhalation after the patient is signaled to stop inhalation. In another embodiment, the detected breathing pattern may be used to determine the time of inhalation to set a pre-set inhalation time in the memory. In this embodiment, aerosol is generated during a portion of the inhalation of the patient. As the user's breathing pattern changes, the pre-set inhalation time may be adjusted.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. A drug delivery apparatus for delivering an aerosol including a drug to a patient while reducing deposition of the aerosol on the apparatus, comprising:
    a mouthpiece portion including:
        a chamber having an air inlet,
        an internal conduit for delivering the aerosol to the patient, the internal conduit having a conduit inlet and a mouthpiece opposite the conduit inlet, wherein the mouthpiece is structured to be received in the mouth of the patient, the mouthpiece portion being further structured such that the patient inhales breathable gas via the air inlet of the chamber into the conduit inlet of the internal conduit and through the mouthpiece of the internal conduit, and
        a flow accelerator disposed within the internal conduit near the conduit inlet, wherein the flow accelerator is a removable insert inserted within the internal conduit, the insert having an orifice; and
    an aerosol generator configured to generate the aerosol from a supply of the drug and further configured and arranged to inject the aerosol into the conduit inlet of the internal conduit of the mouthpiece portion,
    wherein said flow accelerator is structured to increase velocity of a combined flow of substantially all the breathable gas from the air inlet and substantially all the aerosol from the aerosol generator within the internal conduit.

2. The drug delivery apparatus according to claim 1, wherein the insert includes:
    a body structured to be received within the internal conduit near the conduit inlet,
    an outer lip extending around an outer periphery of the body, and
    one or more flanges extending from the outer lip, wherein the one or more flanges are structured to fit over an outside of the conduit inlet to hold the insert in place.

3. The drug delivery apparatus according to claim 1, wherein the conduit inlet is generally circular and has across sectional diameter, and wherein the orifice of the insert is generally circular and has an orifice diameter, wherein the orifice diameter is smaller than the cross sectional diameter of the conduit inlet.

4. The drug delivery apparatus according to claim 1, wherein the conduit inlet is generally circular and has a cross sectional diameter, and wherein a cross-section of the orifice is defined by a first arcuate edge located opposite a second arcuate edge, wherein a degree of curvature of the first arcuate edge is greater than a degree of curvature of the second arcuate edge.

5. The drug delivery apparatus according to claim 4, wherein the insert has a periphery, wherein the second arcuate edge is located closer to the periphery of the insert than said first arcuate edge, and wherein the first arcuate edge is located closer to a center of the insert than the second arcuate edge.

6. The drug delivery apparatus according to claim 5, further comprising a control valve disposed within the mouthpiece portion, wherein the control valve is configured to control inhalation flow, wherein operation of the control valve causes the flow within the internal conduit to be uneven, and wherein orientation and shape of the orifice of the insert are arranged and structured to compensate for unevenness of the flow within the internal conduit.

7. The drug delivery apparatus according to claim 1, wherein the orifice is asymmetrical relative to a center of the insert.

8. The drug delivery apparatus according to claim 1, wherein the flow accelerator is formed integrally as part of the internal conduit.

9. The drug delivery apparatus according to claim 8, wherein the flow accelerator is formed near the conduit inlet.

10. The drug delivery apparatus according to claim 1, wherein increasing the velocity of the combined flow causes a reduction in particle size of the aerosol.

11. The drug delivery apparatus according to claim 1, wherein the aerosol generator includes a mesh plate having a plurality of holes, a horn, and a piezoelectric transducer operatively coupled to the horn for causing the horn to vibrate, wherein vibration of the horn forces the drug through the holes of the mesh plate to form the aerosol.

12. The drug delivery apparatus according to claim 1, wherein the internal conduit is generally cylindrically shaped, and wherein the insert is generally cylindrically shaped and includes a body structured to be received within the internal conduit near the conduit inlet.

13. The drug delivery apparatus according to claim 1, wherein the flow accelerator causes the velocity of the combined flow through the insert to be in the range of approximately 100 cm/sec to approximately 500 cm/sec.

14. A drug delivery apparatus for delivering an aerosol including a drug to a patient while reducing deposition of the aerosol on the apparatus, comprising:
 a mouthpiece portion including:
  a chamber having an air inlet,
  an internal conduit for delivering the aerosol to the patient, the internal conduit having a conduit inlet and a mouthpiece opposite the conduit inlet, and
  a flow accelerator disposed within the internal conduit near the conduit inlet, wherein the flow accelerator is an insert inserted within and removable from the internal conduit, the insert having an orifice, wherein the internal conduit is generally cylindrically shaped, wherein the insert is generally cylindrically shaped and includes:
   a body structured to be received within the internal conduit near the conduit inlet,
   an outer lip extending around an outer periphery of the body, and
   one or more flanges extending from the outer lip, wherein the outer lip is structured to rest on top of the conduit inlet and wherein the one or more flanges are structured to fit over an outside of the conduit inlet to hold the insert in place,
 wherein the mouthpiece is structured to be received in the mouth of the patient, the mouthpiece portion being further structured such that the patient inhales breathable gas via the air inlet of the chamber into the conduit inlet of the internal conduit and through the mouthpiece of the internal conduit; and
 an aerosol generator configured to generate the aerosol from a supply of the drug and further configured and arranged to inject the aerosol into the conduit inlet of the internal conduit of the mouthpiece portion,
 wherein the flow accelerator is structured to increase velocity of a combined flow of substantially all the breathable gas from the air inlet and substantially all the aerosol from the aerosol generator within the internal conduit.

15. A method of delivering an aerosol including a drug to a patient via a drug delivery apparatus while reducing deposition of the aerosol on the apparatus, the method comprising:
 providing a mouthpiece portion including a chamber having an air inlet and an internal conduit, the internal conduit having a conduit inlet, the internal conduit for delivering breathable gas from the air inlet combined with the aerosol through the conduit inlet to the patient, the internal conduit further having a mouthpiece opposite the conduit inlet that is structured to be received in the mouth of the patient, the mouthpiece portion being structured such that the patient inhales through the mouthpiece;
 generating the aerosol from a supply of the drug;
 injecting the aerosol into the conduit inlet of the internal conduit; and
 increasing velocity of a combined flow of substantially all the breathable gas from the air inlet of the chamber and substantially all the aerosol within the internal conduit through a removable insert inserted within the internal conduit and removable from the internal conduit.

16. A method of delivering an aerosol including a drug to a patient via a drug delivery apparatus while reducing deposition of the aerosol on the apparatus, the method comprising:
 providing a mouthpiece portion including a chamber having an air inlet and an internal conduit, the internal conduit having a conduit inlet, the internal conduit for delivering breathable gas from the air inlet combined with the aerosol through the conduit inlet to the patient, the internal conduit further having a mouthpiece opposite the conduit inlet that is structured to be received in the mouth of the patient, the mouthpiece portion being structured such that the patient inhales through the mouthpiece;
 detecting the commencement of inhalation by the patient through the mouthpiece;
 generating the aerosol from a supply of the drug;
 injecting the aerosol into the conduit inlet of the internal conduit for at least a portion of the time that the patient is inhaling through the mouthpiece;
 increasing velocity of a combined flow of substantially all the breathable gas from the air inlet of the chamber and substantially all the aerosol within the internal conduit through a removable insert inserted within the internal conduit and removable from the internal conduit;
 signaling the patient to cease inhalation through the mouthpiece after a pre-set period of time has elapsed from the detection of the commencement of inhalation; and
 adjusting the pre-set period of time for subsequent inhalations through the mouthpiece based upon a time difference between a time that the signaling step is commenced and a time at which the patient actually ceases inhalation through the mouthpiece.

* * * * *